United States Patent [19]

Kline

[11] 4,219,520
[45] Aug. 26, 1980

[54] METHOD OF MAKING THROMBO-RESISTANT NO-THROMBOGENIC OBJECTS FORMED FROM A UNIFORM MIXTURE OF A PARTICULATE RESIN AND COLLOIDAL GRAPHITE

[75] Inventor: William M. Kline, Gloversville, N.Y.

[73] Assignee: Medical Evaluation Devices and Instruments Corp., Gloversville, N.Y.

[21] Appl. No.: 938,051

[22] Filed: Aug. 30, 1978

[51] Int. Cl.² .......................... B44D 1/16; B05D 7/02; B05D 5/04

[52] U.S. Cl. .................................... 264/129; 264/230; 427/2; 3/1.4; 128/DIG. 21; 424/183; 428/409

[58] Field of Search ................. 3/1.4; 427/2; 424/183; 128/DIG. 21; 264/230, 129

[56] References Cited

U.S. PATENT DOCUMENTS

| | | | |
|---|---|---|---|
| 3,549,409 | 12/1970 | Dyck | 424/183 |
| 3,585,647 | 6/1971 | Gajewski | 3/1.4 |
| 3,616,935 | 2/1970 | Love | 424/183 |
| 3,617,344 | 11/1971 | Leeninger | 424/183 |
| 3,639,141 | 2/1972 | Dyck | 3/1 |
| 3,829,903 | 8/1974 | Stati | 3/1 |
| 3,839,743 | 10/1974 | Schwarcz | 3/1.4 |

OTHER PUBLICATIONS

Gott, The Coating of Intravascular Plastic Prostheses with Colloidal Graphite, pp. 382-389.
Nonthrombogenic Materials Via a Simple Coating Process, Grode, vol. XV, Trans. Amer. Soc. Art. Int. Org. 1969, pp. 1-6.
Gott, Techniques of Applying Graphite-Benzalkonium Heparin Coating to Plastics, vol. X, Trans. America Soc. Artif. Int. Organs 1964, pp. 213-217.

*Primary Examiner*—Sam Silverberg
*Attorney, Agent, or Firm*—Thomas E. Tate

[57] ABSTRACT

The disclosure is that of an invention directed to new compositions of matter comprising a mixture of a resin in particulate form and colloidal graphite; and the use of such mixture to form objects of predetermined sizes and shapes, the exposed surfaces of which are strip treated and coated with a cationic surface active agent to make them Heparin-receptive, after which the objects are Heparin-coated to make them thrombo-resistant and non-thrombogenic.

12 Claims, 5 Drawing Figures

METHOD OF MAKING THROMBO-RESISTANT NO-THROMBOGENIC OBJECTS FORMED FROM A UNIFORM MIXTURE OF A PARTICULATE RESIN AND COLLOIDAL GRAPHITE

RELATED APPLICATIONS

Applications Ser. Nos. 155 and 156, both filed on Jan. 2, 1979, are divisions of this application.

THE INVENTION

This invention relates generally to new and useful improvements in the production of flexible materials or objects used within the vascular systems of animate beings and particularly seeks to provide novel compositions of matter that can be used in the manufacture of such flexible materials or objects to make them thrombo-resistant and non-thrombogenic over substantial periods of time.

It is well known that the thrombo-resistant and non-thrombogenic characteristics of objects such as catheters, spring guides, etc., are enhanced if they are made from or coated with a fluorinated hydrocarbon such as a FEP (hexafluoropropylenetetrafluoroethylene copolymer) or TFE (tetrafluoroethylene) resin, commercially available as "Teflon" FEP or "Teflon" TFE from Du Pont. Typical examples of such resin-surfaced objects are described in U.S. Pat Nos. 3,757,768, granted Sept. 11, 1973; 3,922,378, granted Nov. 25, 1975; 4,044,765, granted Aug. 30, 1977; 4,052,989, granted Oct. 11, 1977; and in this inventor's U.S. patent application Ser. No. 893,964, filed Apr. 6, 1978 and directed to an intracardial electrode.

Even though the thrombo-resistant and non-thrombogenic characteristics of such objects are adequate for many purposes, it has become apparent that further improvement is needed, particularly where relatively long retention times may be involved, and this invention is directed to the solution of that problem.

It is also well known that Heparin, a naturally occurring mucopolysaccharide, is an excellent anti-coagulating agent and has been used for that purpose for many years.

Accordingly, the problem may be further described as; how can Heparin be applied and firmly bonded to flexible objects designed for relatively long time retention within the vascular systems of animate beings?

Heretofore, the direct coating of Heparin on flexible surfaces of vascular assist devices has not been considered possible because of the brittle nature of the coatings resulting from the application techniques thereof known to date.

For example, Gott, et al, in a study reported in Vol. X Trans. Amer. Soc. Artif. Int. Organs, 1964, pages 213–217, discovered that when colloidal graphite in a liquid plastic binder is coated on rigid metal and plastic surfaces, certain cationic surface active agents firmly affix themselves to the graphite particles in a non-reversible manner. The resultant surface may then be treated with an aqueous or saline solution of Heparin or Heparin-like compound which adheres to the graphite-cationic base. Although this technique is adapted to rigid surfaces, it is not effective on flexible surfaces due to the brittle nature of the dual coating.

As another example, Grode, et al; in an article titled "Non-thrombogenic Materials via a Simple Coating Process" (Vol. XV Trans. Amer. Soc. Artif. Int. Organs, 1969) describes the Heparinization of finely ground test material by steeping sequentially the test material in a solution of an oil soluble quaternary ammonium salt and then in an aqueous solution of Heparin.

In contrast to and as a difference in kind over such earlier known procedures, I have discovered that it is possible to create Heparin-receptive surfaces on many types of formed plastic objects, particularly those formed from fluorinated hydrocarbons, through the use of a new composition of matter comprising a mixture of a resin in particulate form and colloidal graphite. The mixture is processed into an object of predetermined size and shape by any of the well known forming techniques such as extrusion, blow or injection molding, pressing and heating, or sheeting. The mixture also is capable of being formed into threads or yarns which can be braided, woven, knitted or felted into objects of predetermined size and shape. After an object has been formed from the mixture, its exposed surfaces preferably are treated with metallic sodium to expose surface areas of the colloidal graphite particles at or immediately underlying the exposed surfaces of the object, then the sodium treated surfaces are cleaned and coated with a cationic surface active agent to make the surfaces Heparin-receptive, after which a coating of Heparin may be applied over the catonic coating to make the object truly thrombo-resistant and non-thrombogenic.

Although the compositions of matter generally described in the preceding paragraph are particularly directed to those consisting of a mixture of particulate fluoropolymers and colloidal graphite, it should be understood that for the purposes of this disclosure, other materials in particulate form, such as halogenated hydrocarbons, polyolefins, polyurethanes, vinyls and silicones may be used in place of the fluropolymers with substantially equivalent results.

Even though the compositions of matter disclosed herein and their methods of use are primarily intended to produce flexible objects of predetermined sizes and configuration and having Heparin-receptive surfaces, it should be understood that the techniques involved are equally applicable to rigid objects where Heparin-receptive surfaces are required.

Therefore, an object of this invention is to provide novel compositions of matter, each comprising a mixture of a resin in particulate form and colloidal graphite, that can be formed into flexible objects of predetermined shape and size and then treated to make their exposed surfaces Heparin-receptive.

Another object of this invention is to provide a method of treating the exposed surfaces of objects formed from such compositions of matter with a surface-stripping or etching agent such as metallic sodium to expose surface areas of the graphite particles and then coating the stripped surfaces with a cationic surface active agent to make the surfaces Heparin-receptive, after which a coating of Heparin may be applied thereto to make them thrombo-resistant and non-thrombogenic.

A further object of this invention is to provide objects manufactured from such compositions of matter that are thrombo-resistant and non-thrombogenic.

With these and other objects, the nature of which will become apparent, the invention will be more fully understood by reference to the drawings, the accompanying detailed description and the appended claims.

In the drawings, which are intended to illustrate only one example of many objects that can be formed from the compositions of matter and the techniques herein disclosed:

FIG. 1 is an isometric view of a length of catheter tubing that has been extruded from a composition of matter prepared in accordance with this invention, those graphite particles appearing on the outer surface being shown in solid black and those located slightly below the surface being shown in dotted lines. The size of the graphite particles has been exaggerated in the interest of clarity of illustration;

Figure 1:
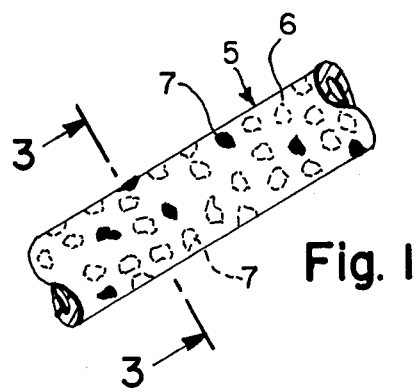

Referring to the drawings in detail the invention, as illustrated, is embodied in a length of lumen-defining catheter tubing generally indicated 5 having a predetermined outside diameter and wall thickness and extruded from a selected resin 6 having colloidal graphite particles 7 uniformly distributed therethrough.

The resin-colloidal graphite composition of matter from which the tubing 5 is extruded comprises from about 99% to about 70% of a resin in dry particulate form selected from the group consisting of halogenated hydrocarbons such as TFE or FEP "Teflon", polyolefins such as polyethylene and polypropylene, polyurethanes, vinyls such as polyvinyl chloride and silicones, and from about 1% to about 30% colloidal graphite of which the particle sizes may range from about 0.5 micron to about 3 microns.

The tubing is continuously extruded and passed through a take off unit which cools and sets the plastic.

Figure 2:
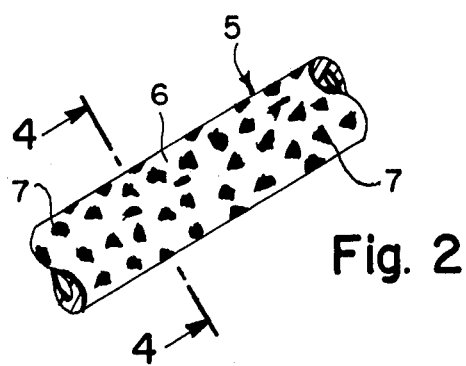
FIG. 2 is a view similar to FIG. 1 but showing the outer surface of the tube as it appears after having been stripped or etched to expose a multitude of the graphite particles.
Figure 3:
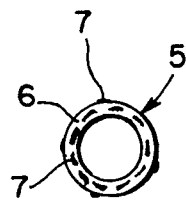
FIG. 3 is a transverse section taken along line 3—3 of FIG. 1.
Figure 4:
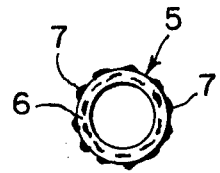
FIG. 4 is a transverse section taken along line 4—4 of FIG. 2.
Figure 5:
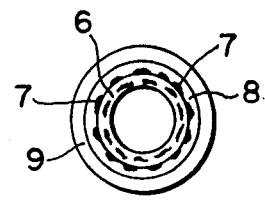
FIG. 5 is a view similar to FIG. 4 but showing the tube when finished by the external sequential applications of cationic surface active agent and Heparin coatings, the internal coatings not being shown.

At this stage only random particles of the colloidal graphite are exposed on the surfaces of the tubing as indicated in FIGS. 1 and 3 and it is necessary to strip or etch the surfaces in order to expose a multitude of the graphite particles as indicated in FIGS. 2 and 4, thus formng a base for a subsequently applied coating of a cationic surface active agent which becomes irreversably bonded thereto.

For this purpose, and if the resin of the tubing is a halogenated hydrocarbon, the tubing from the take off unit is passed through a bath containing metallic sodium dispersed with napthalene in a suitable solvent (such as Ansul 141, a diethyleneglycol dimethylether commercially available from the Ansul Chemical Company) for a period of time ranging from about 1 minute to about 10 minutes, depending on the amount of etch desired. Alternately, this procedure may be carried out with metallic sodium dispersed in liquid ammonia; and in either case the lumen of the tubing may be similarly treated by pumping the sodium dispersion therethrough.

However, if the resin of the tubing is a polyolefin, a polyurethane, a silicone or a vinyl, the stripping or etching should be effected by a hot oxidizing acid such as a combination of sulfuric and chromic acids or a combination of sulfuric acid and sodium dichromate, at about 110°–170° F. for about 1–45 minutes.

The etched tubing then is cleaned with isopropyl alcohol and washed with de-ionized water and dried to complete its preparation for a coating of a cationic surface active agent.

The cleaned, washed and dried tubing then is submersed in a 1–10 to 1–1000 solution of a suitable cationic surface active agent (such as "Zephiran", commercially available from the Sterling Drug Company, or its equivalent) for from about 10 minutes to about 36 hours, depending on the concentration used, and then dried, thus forming a coating 8. At this stage the cationic surface active agent coated tubing is fully Heparin-receptive and may be coated with Heparin by placing the tubing in an aqueous or saline solution of Heparin for from about 1 minute to about 120 minutes, depending on the desired thickness of the Heparin coating, and then dried, thus forming an outer coating 9 and rendering the finished tubing both thrombo-resistant and non-thrombogenic.

The tubing may be made radiopaque if desired by including in the original composition of matter from which the tubing is extruded a small quantity of any of the well known radiopaquing agents, such as bismuth, barium, lead or tin, none of which will react with the graphite particles to degrade the ability of the graphite particles to irreversably accept and bond with the applied coating of the cationic surface active agent.

It also should be understood that it is possible to use intra-vascularly the cationic surface active agent coated tubing without the Heparin coating, in which event the exposed coated surfaces of the tubing will pick up the Heparin from the blood endogenously to naturally create a thrombo-resistant and non-thrombogenic condition. This same endogenous phenomonon is what adds to the retention life of the Heparin-coated tubing because as the Heparin coating might otherwise be depleted, it will continue to be rebuilt naturally.

Further, the tubing is heat-shrinkable when the resin component thereof is a fluoropolymer, such as a FEP or TFE "Teflon", a vinyl or a polyolefin, and can be heat shrunk as a sheathing over and firmly bonded to a flexible inner body, such as a tubular coil spring or braided or woven catheter tubing, and then surface etched and coated as described above to result in a thrombo-resistant non-thrombogenic exterior surface.

I claim:

1. In a method of preparing thrombo-resistant non-thrombogenic objects, the steps of; preparing a uniform mixture of resin in particulate form and colloidal graphite; processing said mixture into an object of predetermined size and configuration and having exposed surfaces; etching the exposed surfaces of said object to expose surface areas of the colloidal graphite particles at or immediately underlying the exposed surfaces of said object; cleaning the etched object; coating the cleaned object with a cationic surface active agent; and applying a coating of Heparin over the cationic surface active agent coating.

2. The method of claim 1 in which said mixture comprises a major portion of said resin and a minor portion of said colloidal graphite.

3. The method of claim 1 in which said mixture comprises from about 99% to about 70% resin and from about 1% to about 30% colloidal graphite; and in which said resin is selected from the group consisting of halogonated bydrocarbons, polyolefins, polyurethanes, silicones and vinyls.

4. The method of claim 3 in which said resin is a fluoropolymer.

5. The method of claim 3 in which said resin is polyethylene.

6. The method of claim 3 in which said resin is polypropylene.

7. The method of claim 3 in which said resin is polyvinylchloride.

8. The method of claim 3 in which said etching is effected by a dispersion of metallic sodium when said resin is a halogenated hydrocarbon.

9. The method of claim 3 in which said etching is effected by a hot oxidizing acid selected from the group consisting of a combination of sulfuric and chromic acids and a combination of sulfuric acid and sodium dichromate.

10. In a method of preparing Heparin-receptive surfaces on objects intended for retention in the vascular systems of animate beings, the steps of; preparing a uniform mixture of resin in particulate form and colloidal graphite; processing said mixture into an object of predetermined size and configuration and having exposed surfaces; etching the exposed surfaces of said object to expose surface areas of the colloidal graphite particles at or immediately underlying the exposed surfaces of said object; cleaning the etched object; and coating the cleaned object with a cationic surface active agent.

11. The method of claim 3 in which said resin is silicone.

12. In a method of forming a flexible tubular object having thrombo-resistant non-thromboginic exterior surfaces the steps of; providing a flexible tubular inner body of predetermined length: preparing an outer flexible tubular sheath having a length at least coextensive with said inner body and formed from a uniform mixture of colloidal graphite and a particulate resin selected from the group comprising halogenated hydrocarbons, polyolefins and polyvinyls; fitting said outer sheath over said inner body; heat shrinking said outer sheath into firmly bonded contact with said inner body; etching the exterior surfaces of said outer sheath to expose a multitude of particles of said colloidal graphite; coating the etched surfaces of said outer sheath with a cationic surface active agent; and applying a coating of heparin over said cationic surface active agent coating.

* * * * *